United States Patent [19]

Treiber et al.

[11] 3,957,845

[45] May 18, 1976

[54] TRIFLUOROMETHYL-SUBSTITUTED PHENYL ACETONITRILES

[75] Inventors: Hans-Jorg Treiber, Bruhl; Ferdinand Dengel, Wilhelmsfeld, both of Germany

[73] Assignee: Knoll A.G. Chemische Fabriken, Ludwigshafen (Rhine), Germany

[22] Filed: Sept. 14, 1970

[21] Appl. No.: 72,131

Related U.S. Application Data

[63] Continuation-in-part of Ser. No. 555,955, June 8, 1966, abandoned, which is a continuation-in-part of Ser. No. 190,772, April 27, 1962, Pat. No. 3,261,859.

[52] U.S. Cl. .............................. 260/465 E; 424/304

[51] Int. Cl.² ..................................... C07C 121/78
[58] Field of Search ................................. 260/465 E

[56] References Cited
UNITED STATES PATENTS 3,261,859    7/1966    Dengel............................... 260/465

*Primary Examiner*—Lewis Gotts
*Assistant Examiner*—Dolph H. Torrence
*Attorney, Agent, or Firm*—Weiser, Stapler & Spivak

[57] ABSTRACT

Basically substituted phenylacetonitriles having also a trifluoromethyl substituent. The compounds are useful as coronary dilators.

9 Claims, No Drawings

TRIFLUOROMETHYL-SUBSTITUTED PHENYL ACETONITRILES

This patent application is a continuation-in-part of patent application Ser. No. 555,955, filed June 8, 1966, now abandoned, which in turn is a continuation-in-part of application Ser. No. 190,772, filed April 27, 1962, entitled Basically Substituted Phenyl Acetonitrile Compounds, now U.S. Pat. No. 3,261,859.

The present invention concerns new fluoro-substituted-phenyl acetonitriles which are valuable in the treatment of circulatory diseases and their pharmaceutical compositions. These compounds alone and in combination are valuable coronary dilators with minimum effect on the blood pressure. The compounds of the invention are also valuable in combating various pathogens, in particular bacterial pathogens. The present invention further concerns pharmaceutical compositions comprising certain basically substituted phenyl acetonitrile compounds which are valuable in the treatment of circulatory diseases by causing dilation of the coronary vessels. The compositions of the invention are useful in the treatment of disturbances of coronary circulation to increase the blood flow in coronary vessels and, concurrently to increase the oxygen content of the venous heart blood.

The invention provides a new and distinct valuable class of fluoro-substituted phenyl acetonitriles which may be represented by the following generic formula I.

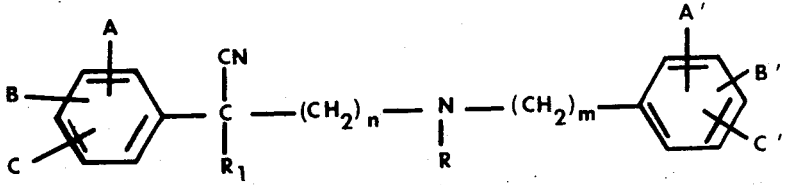

in which R is a lower aliphatic hydrocarbon, such as alkenyl or alkyl;

$R_1$ is a lower alkyl, a cyclic, inclusive of bicyclic saturated or unsaturated hydrocarbon radical, the benzyl or phenyl radical, or the substituted benzyl, or the phenyl radical

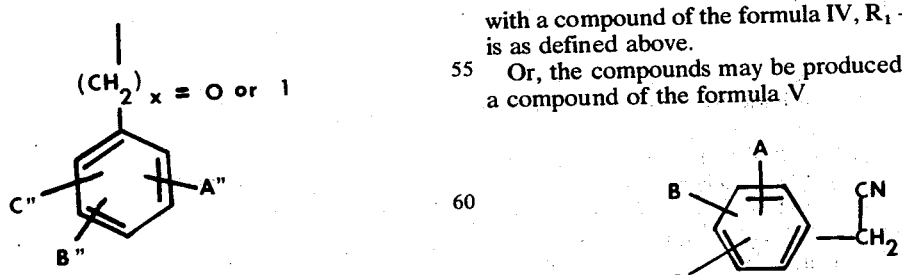

wherein A, B, C, A', B', C', A'', B'', C'' are selected from halogens, lower alkoxy, lower alkyl, hydrogen and wherein at least two of the adjacent substituents A to C, A' to C', and A'' to C'' form a methylene dioxy bridge, and at least one A to C, A' to C', and A'' to C'' is the trifluoromethyl, $CF_3$, radical, n is any integer from two to four, m is any integer from one to three with the further proviso that the trifluoromethyl group is linked at a position other than the ortho position, and the pharmaceutically acceptable acid addition salts. The invention also provides the optical isomers of these compounds, its mixtures including its racemates.

The compounds in which one trifluoromethyl radical is linked to the acetonitrile residue form a most desired class by virtue of their high effectiveness as coronery dilator. Also, the compounds in which m is 2 or 3 are preferred.

The compounds of the invention are obtainable through a number of suitable methods. They can be prepared by reacting a phenyl acetonitrile of the formula I

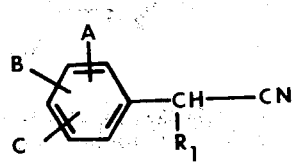

with a compound of the formula II

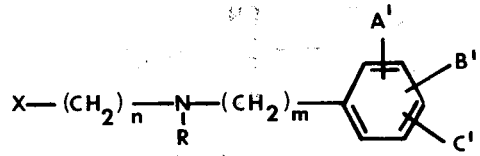

wherein X is a reactive acid residue, preferably a halogen, in the presence of a basic condensing agent which is capable of binding the acid split off during the reaction.

Alternatively the compounds may be produced by reacting a compound of the formula III

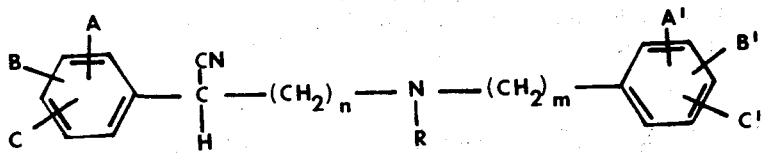

with a compound of the formula IV, $R_1 - X$ wherein X is as defined above.

Or, the compounds may be produced by condensing a compound of the formula V with the compound of formula II as stated above and a compound of formula IV as given above in any desired order whereby it is not necessary to isolate the resulting intermediate products of formula I or III.

Alternatively the compounds may be produced by reacting a compound of the formula VI

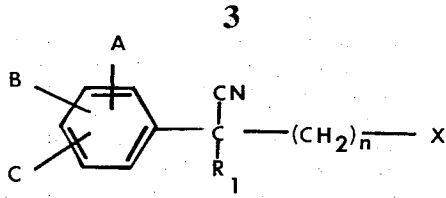

wherein X is as defined above, with a compound of the formula VII

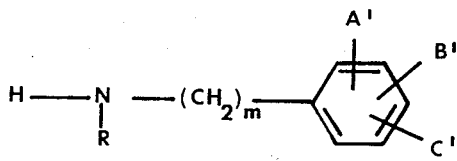

Or, the compounds may be prepared by reacting a phenyl acetonitrile of the formula VIII

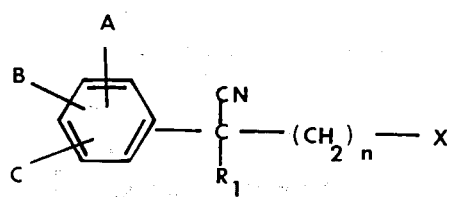

wherein X is as defined above, with an amine of the formula IX

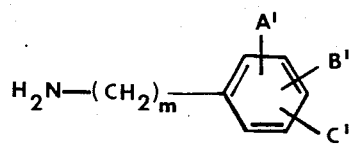

and by introducing the radical R into the resulting secondary amine by suitable alkylation.

In the above formulas the substituents A, B, and C; A', B', and C', A'', B'', and C''; $R_1$, R: n and m are defined above, wherein at least one of A to C, A' to C' and A'' to C'' is a trifluoromethyl radical.

For supplementary description of the method of preparation, reference is made to the above-identified application which is incorporated herein by reference.

The invention also provides a group of valuable compounds of the formula X

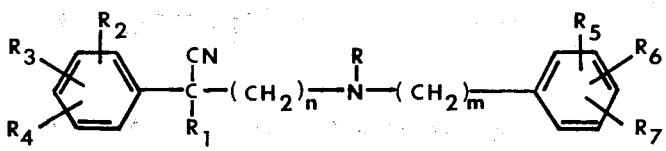

wherein R is a lower aliphatic hydrocarbon, such as alkyl or alkenyl;

$R_1$ is a lower alkyl, a cyclic or bicyclic saturated or unsaturated hydrocarbon radical, such as bicycloalkyl or cycloalkenyl as of 5 to 7 carbon atoms, or bicycloalkenyl; the benzyl or phenyl radical;

$R_2$, $R_3$, $R_4$, $R_5$, $R_6$, and $R_7$ are, each one, hydrogen, chlorine, alkyl, preferably lower alkyl, lower alkoxy, two of said alkoxy on adjacent carbon atoms forming the methylene dioxy group:

m is one of the integers 2 to 3;

n is an integer from 2 to 4;

as the pharmaceutically acceptable acid addition salts thereof.

The above compounds include amongst others the following valuable acetonitrile:

α-(Bicyclo[2,2,1]heptene-5-yl-2-methyl)-α-[(N-methyl-N-benzyl)-β-amino ethyl]phenyl acetonitrile, α-Isopropyl- -[(N-methyl-N-4,5-dioxymethylene phenyl-β-ethyl)-γ-amino propyl]-3,4-dimethoxy phenyl acetonitrile, α-Isopropyl-α-[(N-methyl-N-homoveratryl)-β-amino ethyl]-3,4-dioxymethylene phenyl acetonitrile, α-Isopropyl-α-[(N-methyl-N-homoveratryl)-γ-amino propyl]-3-chloro-4-ethoxy phenyl acetonitrile, α-Isopropyl-α-[(N-methyl-N-homoveratryl)-γ-amino propyl]-phenyl acetonitrile, α-[(N-methyl-N-homoveratryl)-γ-amino propyl]-α,α-diphenyl acetonitrile, α-Isopropyl-α-[(N-methyl-N-homoveratryl)-β-amino ethyl]-3,4-dimethoxy phenyl acetonitrile, α-Isopropyl-α-[(N-methyl-N-homoveratryl)-γ-amino propyl]-3,4-dimethoxy phenyl acetonitrile, α-Isopropyl-α-[(N-methyl-N-homoveratryl-γ-amino propyl]-3,4-dimethoxy phenyl acetonitrile, α-Isopropyl-α-[(N-methyl-N-homoveratryl)-γ-amino propyl]-3,4-dimethoxy phenyl acetonitrile, α-Isopropyl-α-[(N-methyl-N-4-chloro phenyl-β-ethyl)-γ-amino propyl]-3,4-dimethoxy phenyl acetonitrile, α-Isobutyl-α-[(N-methyl-N-homoveratryl)-β-amino ethyl]-3,4-dimethoxy phenyl acetonitrile, α-Isopropyl-[(N-ethyl-N-benzyl)-γ-amino propyl]-3,4-dimethoxy phenyl acetonitrile, α-Isobutyl-α-[(N-methyl-N-homoveratryl)-α-amino propyl]-3,4-dimethoxy phenyl acetonitrile, α-[(N-Methyl-N-homoveratryl)-γ-amino propyl]-phenyl acetonitrile, and α-[(N-methyl-N-homopiperonyl)-γ-amino propyl]-3,4-dimethoxy phenyl acetonitrile.

These substituted acetonitriles can be prepared as disclosed in the parent application Ser. No. 190,772, which is incorporated herein by reference, especially all examples, including Examples 3,4,23,25 and 26.

All compounds shown in said application can be trifluoromethyl substituted in the position indicated by formula I, above.

The invention is illustrated by the following examples which are not to be construed as limitation on the invention.

EXAMPLE 1

There are dissolved in 200 ml. of toluene 22.7 g. (0.1 mole) of α-Isopropyl-3-trifluoromethyl phenyl acetonitrile in a three-necked flask provided with stirrer, reflux condenser and dropping funnel and heated with a solution of 1-chloro-3-(N-methyl-N-β-3-trifuoromethyl phenyl ethyl)-aminopropane in 200 ml. of toluene. At 90°C., 13 g. of a 30% suspension of sodium amide in toluene are added over a period of 20 minutes and the mixture is subsequently heated to boiling for 4 hours.

To the cooled solution there are added 200 ml. water, the toluene layer is separated, dried with anhydrous magnesium sulfate, the toluene is distilled off, and the residue is fractionated in vacuo.

There is obtained 41.2 g. of α-Isopropyl-α-[(N-Methyl-N-β-3-trifluoromethyl phenyl ethyl)-γ-aminopropyl)-3-trifluoromethyl phenyl acetonitrile as a yellow, viscous oil in a yield of 88% of theory. Its boiling point is 205°–210°C at 0.1 mm. Hg. The acid oxalate prepared therefrom has a melting point of 188°C.

The starting reactants were prepared by condensation of 3-trifluoromethyl phenyl acetonitrile with isopropyl bromide, or by liberating the chlorine base from the corresponding acid oxalate.

EXAMPLE 2

Following the procedure described in Example 1, 93.6 g. (0.223 mole) of α-[(N-Methyl-N-homoveratryl)-γ-aminopropyl]-3-trifluoromethyl phenyl acetonitrile are dissolved in 500 ml. of toluene, 30.8 g. (0.25 mole) isopropyl bromide are added and 32.5 g. of a 30% sodium amide suspension in toluene are slowly added dropwise at 70°C. Subsequently the mixture is held at boiling for 3 hours, cooled, 150 ml. water are added, and the separated toluene layer is extracted twice with water. This fraction is dried with anhydrous magnesium sulfate, the toluene is removed and the residue fractionated.

There is obtained 89.5 g. of α-Isopropyl-α-[(N-metyl-N-homoveratryl)-γ-aminopropyl]-3-trifluoromethyl phenyl acetonitrile as a yellow, viscous oil in a yield of 87% of theory. Its boiling point is 195°–200°C at 0.1 mm. Hg. Its acid oxalate melts at 158°–159°C.

The starting reactant is prepared by condensation of 3-trifluoromethyl phenyl acetonitrile and N-Methyl-N-homoveratrylamino-γ-chloropropane in the presence of sodium amide.

EXAMPLE 3

30 g. (0.1 mole) of α-Isopropyl-α-(3'-chloropropyl)-3-trifluoromethyl phenyl acetonitrile and 39 g. (0.2 mole) of N-Methylhomoveratryl amine are heated in an oil bath at 130°–150°C for 7 hours. After the residue has solidified to a glassy mass, it is treated hot with 1 liter of benzene, whereupon the hydrochloride of N-methylhomoveratryl amine precipitates and is filtered off by suction. The filtrate is washed with 10% sodium hydroxide and dried with anhydrous magnesium sulfate; the benzene is distilled off and the residue fractionated.

There is obtained 36.5 g. of α-Isopropyl-α-[(N-methyl-N-homoveratryl)-γ-aminopropyl]-3-trifluoromethyl phenyl acetonitrile as a yellow, viscous oil in a yield of 79% of theory, The boiling point is 195°–200°C at 0.1 mm. Hg. Its acid oxalate melts at 158°C. The salt is identical with the oxalate described in Example 2. The starting acetonitrile reactant is prepared by condensation of 1-chloro-3-bromopropane or 1,3-dichloropropane with α-Isopropyl-3-trifluoromethyl phenyl acetonitrile in the presence of sodium amide.

EXAMPLE 4

45 g. (0.15 Mole) of α-Isopropyl-α-(3'-chloropropyl)-3-trifluoromethyl phenyl acetonitrile and 55 g. (0.3 mole) of homoveratryl amine are heated to 130°–150°C for 7 hours. After the residue has solidified to a glassy mass, it is treated hot with 1 liter of benzene, whereupon the hydrochloride of homoveratryl amine precipitates and is filtered off by suction. The filtrate is washed with 10 % sodium hydroxide and dried with anhydrous magnesium sulfate, the solvent is distilled off an the residue fractionated.

There is obtained 45 g. of α-Isopropyl-α-[(N-methyl-N-homoveratryl)-γ-aminopropyl]-3-trifluoromethyl phenyl acetonitrile as a yellow, viscous oil in a yield of 68 % of theory. Its boiling point is 203°–208°C at 0.1 mm. Hg. Melting point of the acid oxalate 154°C.

EXAMPLE 5

There are dissolved 45 g. of the secondary base obtained in 100 ml. methanol and 40 ml. of 35 % aqueous formaldehyde and methylated by addition of portions of sodium borohydride totaling 7.5 g. (0.2 mole) while hot. In the course of the reaction, the temperature of the solution rises to boiling. The mixture is then stirred for another 2 hours without further heating. The methanol solution is evaporated to dryness; to the residue there is added 200 ml. of water, and it is extracted with ether. The dried ether solution is again evaporated to dryness and the residue distilled.

There is obtained 30.5 g. of α-Isopropyl-α-[(N-methyl-N-homoveratryl)-γ-aminopropyl]-3-trifluoromethyl phenyl acetonitrile as a yellow, viscous oil in a yield of 66 % of theory. Its boiling point is 195°–200°C at 0.1 mm. Hg. Its acid oxalate melts at 158°C. The salt is identical with the oxalate described in Examples 2 and 3.

The methylation may hydrogenation be carried out with formaldehyde-formic acid solution or by hydenation in the presence of palladium or nickel catalyst or amalgamated aluminum.

EXAMPLES 6–12

The following fluoro-substituted phenyl acetonitriles are obtained in a like manner, the yields being indicated in percent of theory. The respective boiling points are stated, followed by the melting point of the oxalate.

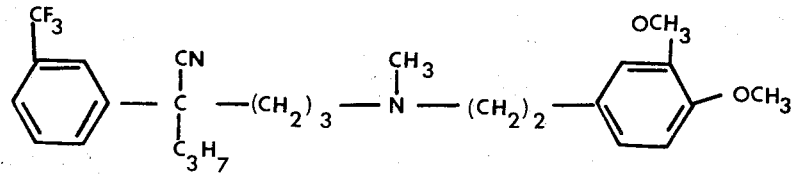

70% yield; 195°–200°C at 0.1 mm. Hg.; 158°C

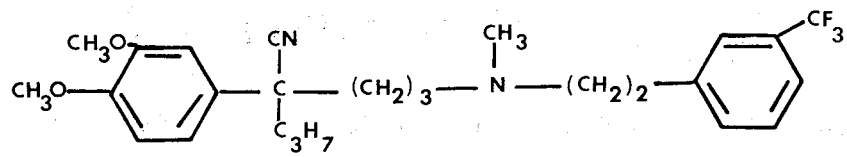

62% yield; 195°–200°C at 0.1 mm. Hg; 147°C.

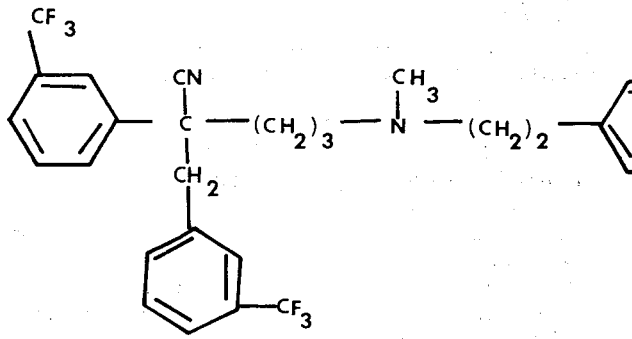

51% yield; 232°–235°C at 0.3 mm. Hg; 79°C

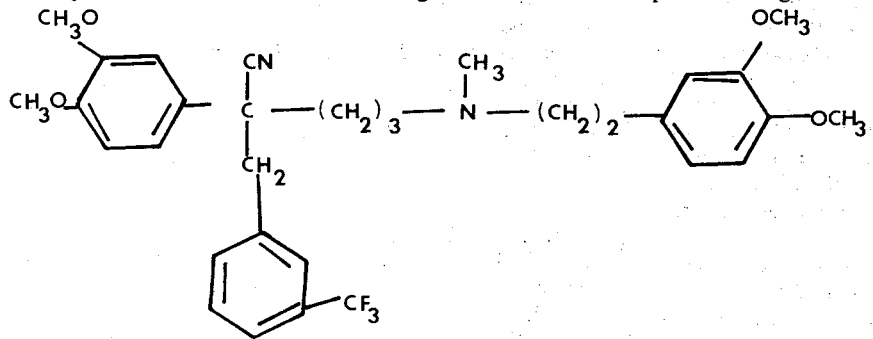

66% yield; 235°–240°C at 0.05 mm. Hg., 105°C (decomp.)

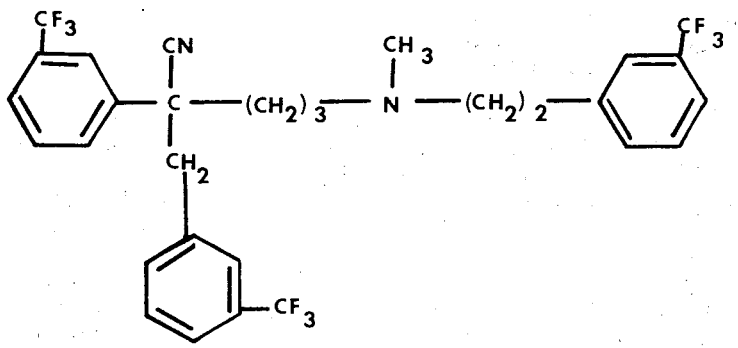

59% yield; 207°–210°C at 0.01 mm. Hg.; 142°C

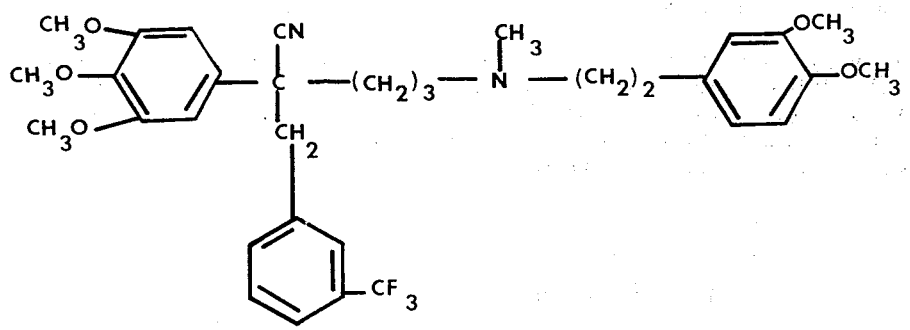

39% yield; 210°–215°C at 0.01 mm. Hg.; 111°C

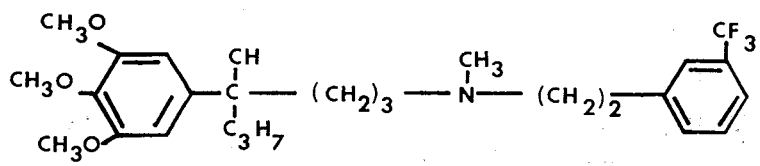

56 % yield; 202°–204°C at 0.1 mm. Hg.; 121°C.

The compounds of the invention possess valuable pharmacological effects, especially as coronary dilators. The trifluoromethyl substituted compounds distinguish themselves by their coronary dilator properties accompanied with a minimum of a lowering of blood pressure and of toxic side effects. Preferred components include:

α-isopropyl -[(N-methyl-N-homoveratryl)-α-aminopropyl]-3-trifluoromethyl phenyl acetonitrile, α-isopropyl-α-[(N-methyl-N-β-3-trifluoromethyl phenyl ethyl)-γ-aminopropyl]-3-trifluoromethyl phenyl acetonitrile, and α-isopropyl- α-[(N-methyl-N-β-3-trifluoromethyl phenyl ethyl)-γ-aminopropyl]-3,4-dimethoxyphenyl acetonitrile.

Pharmacological and chemical data show that the compounds of the present invention increase the blood flow in the coronary vessels, the oxygen content of the venous heart blood while keeping the blood pressure substantially constant.

The coronary blood flow was determined by standard methods on dogs., namely by means of the sinus balloon catheter or by means of Shiply's rotameter in dogs with exposed thorax, or by means of a heart catheter in dogs with closed thorax. It was found that dilation of the coronary vessels sets in on intravenous administration of 0.03 mg./kg. Coronary dilatation is pronounced with 0.125 mg./kg. and surpasses several times the effect of papaverine. theophylline, and other coronary dilators. With α-isopropyl-α-[(N-methyl-N-homoveratryl)-γ-aminopropyl]-3-trifluoromethyl phenyl acetonitrile, a steep increase in the coronary blood flow is observed 30 seconds to 60 seconds after injection. The maximum is attained after 60 seconds to 120 seconds within a relatively short period of time. Said maximum remains substantially unchanged for a prolonged period of time. Administration of 0.06–0.125 mg./kg. causes an increase in blood flow amounting to 100 % to 300 %. Within about 5 minutes to 15 minutes the coronary blood flow returns to its initial value. Thus optimum effects are achieved on intravenous administration of 0.06 mg./kg. to 0.125 mg./kg. An increase in oxygen content of coronary sinus blood is also increased. Subsequently a decrease to its initial value of the venous oxygen content corresponding to the coronary blood flow is observed. The oxygen content of the arterial blood does not show significant changes. Standard tests show no adverse effects on heart metabolism. Other standard tests and evaluation of the compounds show the remarkable absence of toxic side effects.

The compounds of the present invention are preferably administered orally. A dose of one to two tablets containing about 20 mg. thereof three times daily has proved to produce satisfactory results. The maintenance dose is about one tablet of about 20 mg. given three times daily. The dose may vary, of course. The daily dose is between about 30 mg. and about 250 mg. provided in three to four single doses.

Intravenous and intramuscular injection or rectal application in the form of suppositories may also be employed as mode of administration. For injections aqueous or saline solutions can be used. The new compounds of the present invention may be administered orally in the form of tablets, pills, powders, capsules, solutions, emulsions, suspensions, dispersions, and in other suitable form.

In the case of powders, fine, uniform dispersions of the new compounds is preferable. Such dispersion can be achieved, for instance, by making and milling the new compounds with a solid, pulverulent extending agent to the desired fineness, or by impregnating the already milled, finely powdered, solid carrier with a solution of the active compound in water, or a water-miscible solvent and then removing the water or solvent. As solid carriers, which are suitable for the manufacture of useful pharmaceutical preparations, various inert pulverulent distributing agents as they are conventionally used in pharmaceutical compounding may be employed. When preparing tablets, pills, powders, and the like, the commonly used diluting agents, binders, lubricants, and the like are added, such as sugar, lactose, talcum, starch, pectins; as binders gelatin, gum arabic methyl cellulose, yeast extract, agar, tragacanth; and as lubricating agents, magnesium stearate, stearic acid, and others.

It is understood that other acid addition salt than those mentioned and described hereinabove may be prepared for instance, acid addition salts with sulfuric acid, sulfamic acid, phosphoric acid, hydrobromic acid, and other inorganic acids as well as with succinic acid, tartaric acid, malonic acid, maleic acid, malic acid, benzoic acid, phthalic acid, nicotinic acid, and other organic acids, provided the respective salts are pharmaceutically acceptable and substantially well tolerated in the doses administered.

Moveover, the compounds of the invention may be used in combating bacterial, protozoal, viral, helmintic, or fungal pathogens such as *Escherichia coli*, *Staphylococous aureus*, and others. In combating bacterial infections, the compounds of the invention may be administered orally or parenterally by incorporating therapeutic effective amounts in conventional carriers. Useful dosages are adapted to the use and effect intended and may range from about 0.01 to 1 % or more, in a suitable liquid or solid carrier, in the optional presence of a surface active compound. The fluoro-substituted compounds of the invention may be used in combating pathogenic infections, e.g. bacterial in warm blooded animals. inclusive of humans. They are also useful in general household or industrial as general disinfectants and sanitary purposes.

When compared with the substituted acetonitriles disclosed in the parent application Ser. No. 190,772 the new class of fluoro-substituted phenylacetonitriles show significant differences with respect to their heart action. While α-Isopropyl-α-[(N-methyl-N-homoveratryl)-γ-amino propyl]-3,4-dimethoxy phenyl acetonitrile causes a limited increase of heart rate to the detriment of a shortened conduction time and a shortened ventricular complex and leaves the oxygen consumption unchanged, in contrast the α-Isopropyl-α- [(N-methyl-N-homoveratryl)-γ-aminopropyl]-3-trifluoromethyl phenyl acetonitrile primarily causes a frequency increasing or decreasing effect dependent upon the dosage used through a shortening of the conduction time. Also, the oxygen consumption shows a dependency on dosage, an increase being noted with small dosages and a decrease with large dosages. The dependency of the intermediate blood pressure drop on dosage results with α-Isopropyl-α-[(N-methyl-N-homoveratryl)-γ-aminopropyl]-3,4-dimethoxy phenyl acetonitrile from the decrease of the aystolic pressure, whereas for α-Isopropyl-α-[(N-methyl-N-homoveratryl)γ-aminopropyl]-3-trifluoromethyl phenyl acetonitrile it results from the diastolic pressure. Moreover, while α-Isopropyl-α-[(N-methyl-N-homoveratryl)-γ-aminopropyl]-3,4-dimethoxy phenyl acetonitrile decreases the isoproterenol effect in dependency on dosage, in case of the α-Isopropyl-α-[(N-methyl-N-homoveratryl)-γ-aminopropyl]-3-trifluoromethyl homoveratryl)-γ-aminopropyl]-3-trifluoromethyl phenyl acetonitrile there is observed a pronounced change of the isoproterenol blood pressure reaction to a distinct reversal to a blood pressure increase.

There is another class of desirable compounds which have at least one fluoro atom as a substituent for A, B, C, A', B', C', and A'', B'', C''; also $R_1$, in formula I, can be substituted phenyl or benzyl, such as with Cl or methoxy groups. Further, the alkylene groups —$(CH_2)_n$— and —$(CH_2)_m$— can be branched i.e. substituted with various aliphatic, e.g. alkyl groups. Moreover, A, B, or C, or A', B', C' and A'', B'' and C'' can be a hydroxyl group. Examples of this compound are the following: α-Isopropyl-α-[(N-methyl-N-3-fluoro-4-methoxy-8-phenyl ethyl)-γ-amino propyl]-3-fluoro-4-methoxy phenyl acetonitrile, α-4-Chlorobenzyl-α-[(N-methyl-N-homoveratryl)γ-amino propyl]-4-chloropropyl acetonitrile, α-3,4-Dimethoxy benzyl-α-[(N-methyl-N-homoveratryl)-γ-amino propyl]-4-chlorophenylacetonitrile, α-4-Chlorobenzyl-α-[(N-methyl-N-β,β-diisopropyl-β-3,4-dimethoxy phenyl ethyl)-γ-amino propyl]-4-chlorophenyl acetonitrile, α-Isopropyl-α-[(N-methyl-N-4-methoxy-β-phenyl propyl)-γ-amino propyl]-3,4-dimethoxy phenyl acetonitrile, α-(4-Chlorobenzyl)-α-[(N-methyl-N-3,4-dihydroxy-β-phenyl ethyl)-γ-amino propyl]-4-chlorophenyl acetonitrile, α-Isopropyl-α-[(N-methyl-N-3-hydroxy-4-methoxy-β-phenyl ethyl)-γ-amino propyl]-3,4-dimethoxy phenyl acetonitrile, α-Isopropyl-α-[(N-methyl-N-3,4-dihydroxy-β-phenyl ethyl)-γ-amino propyl]-3,4-dihydroxy phenyl acetonitrile, α-3,4-Dimethoxy phenyl-α-[(N-benzyl-γ-amino propyl]-3,4-dimethoxy phenyl acetonitrile.

We claim:

1. The substituted phenyl-acetonitrile of the formula

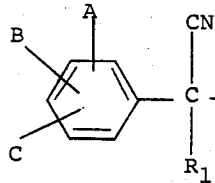 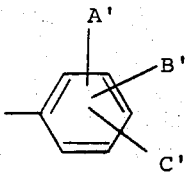

wherein R is methyl, m is 2, as is 3 and when one of the substituents A, B and C is trifluoro methyl, the other two substituents are each hydrogen, when two of the substituents are methoxy, the other substituent is hydrogen, or all three substituents are methoxy, and when one of A', B' and C' is trifluoromethyl the other two substituents are each hydrogen, and when two of the substituents are methoxy, the other substituent is hydrogen, or all three substituents are hydrogen; and $R_1$ is isopropyl or trifluoro methylbenzyl with the proviso that at least one of A, B, C, A', B', or C' be a trifluoro methyl substituent in a position other than in the ortho-position on the ring, and the pharmaceutically acceptable acid addition salts.

2. The compound of claim 1 wherein of the substituents A, B and C, one is trifluoro methyl and the other two are hydrogens.

3. The compound of claim 1 wherein $R_1$ is trifluoromethylbenzyl

4. The compound of claim 1 wherein of the substituents A', B' and C', one is trifluoro methyl and the other two are hydrogens.

5. The compound of claim 1 which is alpha-isopropyl-alpha-[(N-methyl-N-homoveratryl)-gamma-aminopropyl]-3-trifluoromethyl phenyl acetonitrile.

6. The compound of claim 1 which is alpha-isopropyl-alpha-[(N-methyl-N-beta-3-trifluoromethyl phenyl ethyl)-gamma-aminopropyl]-3-trifluoromethyl phenyl acetonitrile.

7. The compound of claim 1 which is alpha-3-trifluoromethylbenzyl-alpha-[(N-methyl-N-homoveratryl)-gamma-aminopropyl]-3-trifluoromethyl phenyl acetonitrile.

8. The compound of claim 1 which is alpha-isopropylalpha-[(N-methyl-N-beta-3-trifluoromethyl phenyl ethyl)- gammaaminopropyl]-3,4-dimethoxy phenyl acetonitrile.

9. The compound of claim 1 which is alpha-isopropylalpha-[(N-methyl-N-beta-3-trifluoromethyl phenyl ethyl)-gamma-aminopropyl]-3,4,5-trimethoxyphenyl acetonitrile.

* * * * *